United States Patent
Breffa et al.

(10) Patent No.: US 8,575,372 B2
(45) Date of Patent: Nov. 5, 2013

(54) ISOSORBIDE DERIVATIVES

(75) Inventors: Catherine Breffa, Düsseldorf (DE); Hans-Christian Raths, Monheim (DE); Thorsten Löhl, Bonn (DE)

(73) Assignee: Cognis IP Management GmbH, Duesseldorf (DE)

( * ) Notice: Subject to any disclaimer, the term of this patent is extended or adjusted under 35 U.S.C. 154(b) by 202 days.

(21) Appl. No.: 13/123,666

(22) PCT Filed: Sep. 30, 2009

(86) PCT No.: PCT/EP2009/007015
§ 371 (c)(1),
(2), (4) Date: Apr. 12, 2011

(87) PCT Pub. No.: WO2010/040464
PCT Pub. Date: Apr. 15, 2010

(65) Prior Publication Data
US 2011/0237809 A1    Sep. 29, 2011

(30) Foreign Application Priority Data
Oct. 9, 2008 (EP) .................... 08017704

(51) Int. Cl.
*C07D 493/00* (2006.01)
(52) U.S. Cl.
USPC ........................................ 549/464
(58) Field of Classification Search
USPC ........................................ 549/464
See application file for complete search history.

(56) References Cited

U.S. PATENT DOCUMENTS

2002/0174596 A1* 11/2002 Deflort et al. ............ 44/351

FOREIGN PATENT DOCUMENTS

EP    0186276    7/1986
EP    1106616    6/2001

OTHER PUBLICATIONS

Peter R. Ashton et al.: Molecular Meccano, 51 [ ]Diastereoselective Self-Assembly of [2] Catenanes. In: Eur. J. Org. Chem. 1999, pp. 995-1004.
Hoang Vu Dang et al: Composition analysis of two batches of polysorbate 60 using MS and NMR techniques. In: Journal of Pharmaceutical and Biomedical Analysis 40 (2006) pp. 1155-1165.

* cited by examiner

*Primary Examiner* — Taylor Victor Oh
(74) *Attorney, Agent, or Firm* — Diehl Servilla LLC

(57) ABSTRACT

Disclosed are derivatives of isosorbide having formula (I)

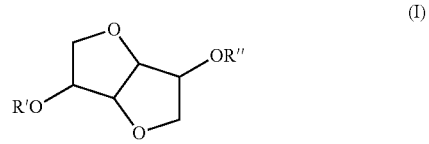

wherein R' and R" represent hydrogen or a polymeric ether moiety $(CH_2-CHR_1-O)_x-H$, where $R_1$ represents hydrogen, or an alkyl or alkenyl moiety having 1 to 33 carbon atoms, which is saturated or unsaturated, branched or linear. This polymeric ether moiety can be a homopolymer or a copolymer, with x being the total degree of polymerization (DP). Preferred is a block copolymer composed of monomer A (DP=a), preferably ethylene oxide or propylene oxide, and monomer B (DP=b), preferably a saturated or unsaturated, branched or linear alkyl or alkenyl moiety having 1 to 33 carbon atoms, where x=a+b. x is a number from 0 to 50, with the proviso that R' and R" are not both hydrogen. The isosorbide derivatives are useful as components of detergent, cleanser, cosmetic and agricultural compositions.

9 Claims, No Drawings

ISOSORBIDE DERIVATIVES

CROSS-REFERENCE TO RELATED APPLICATIONS

The present application is the national stage application under 35 USC §371 of international patent application number PCT/EP2009/007015, filed on Sep. 30, 2009, which claims the benefit of priority of European application number EP08017704.1, filed on Oct. 9, 2008, the entire contents of both of which are incorporated herein by reference.

FIELD OF THE INVENTION

The present application pertains to derivatives of isosorbide, in particular isosorbide ethers, and particularly hydroxyalkyl ether derivatives thereof, as well as to methods for the preparation of these derivatives.

BACKGROUND OF THE INVENTION

Isosorbide (or 1,4:3,6-dianhydrosorbitol, see formula below) is the anhydride of sorbitol.

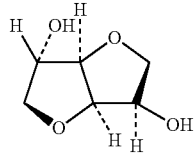

Upon heating sorbitol with an acid, for example concentrated sulfuric or hydrochloric acid, two molecules of water are eliminated with the formation of isosorbide. These compounds are also known generally as dianhydrohexitols (including besides isosorbide, the isomers isomannide and isoidide). Besides isosorbide, certain derivatives of isosorbide are well known, inter alia mono- and diesters, and ethers, in particular, mono- and dimethylethers of isosorbide. Those ethers are known to have good solvent properties for pharmaceutical and cosmetic compositions. EP 186 276 A2 discloses C1-C4 alkyldiethers of isosorbide, useful in oral hygiene preparations. The document discloses both symmetrical as well as unsymmetrical ethers. A process for the preparation of such ethers is disclosed in EP 315 334 A2, using dialkylcarbonates and a basic catalyst to etherify the isosorbide. Chatti et al. reported in Recent Res. Devel. Organic Chem., 7 (2003): 13-20 ISBN: 81-7895-093-6, a method to prepare various dialkylethers of isosorbide using microwave irradiation. Simple isosorbide ethers are also known to be suitable in personal care applications, as disclosed in EP 1 216 685 A2.

Since isosorbide is derived from natural sources, by the double dehydration of starch, it is an interesting way to obtain new compounds based on renewable resources. In the fields of cosmetics, pharmaceuticals and home products, there is a continuing search for new derivatives with new properties to meet the needs of the application areas.

DETAILED DESCRIPTION OF PREFERRED EMBODIMENTS

The present application pertains in a first embodiment to an isosorbide derivative, according to general formula (I)

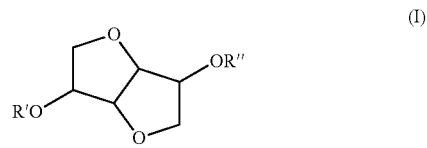

wherein R' and R" independently from each other represent a hydrogen atom or a polymeric ether moiety ($CH_2$—$CHR_1$—$O)_x$—H. This polymeric ether moiety is composed of epoxide-based monomers, described as $H_2COCH$—$R_1$, where $R_1$ represents in the broadest sense either a hydrogen atom, or an alkyl or alkenyl moiety with 1 to 33 carbon atoms, which can be saturated or unsaturated, branched or linear.

Preferably $R_1$ is a linear or branched, saturated or unsaturated alkyl or alkenyl moiety containing 1 to 33 carbon atoms. The polymeric ether moiety can be a homopolymer or a copolymer, x being the total degree of polymerization (DP). Preferred is a block copolymer composed of monomer A (DP=a), preferably ethylene oxide or propylene oxide, and monomer B (DP=b), preferably an alkyl or alkenyl moiety with 1 to 33 carbon atoms, which is saturated or unsaturated, branched or linear, where x=a+b. x is zero, or a number from 1 to 50. Formula (I) represents compounds of the invention, with the proviso is that R' and R" are not both hydrogen atoms. In a preferred embodiment R'=R"=($CH_2$—$CHR_1$—$O)_x$—H.

In the case where the moieties R' and/or R" represent a group ($CH_2$—$CHR_1$—$O)_x$—H, with $R_1$=H or —$CH_3$, an alkoxylated isosorbide derivative is present. Preferably $R_1$ is a hydrogen atom, and then this compound is an ethoxylated isosorbide. Besides the ethoxylated isosorbides, propoxylated isosorbides are also encompassed, as well as mixed alkoxylates, containing both ethylenoxide and propylenoxide moieties, either as blocks or in random manner.

Preferred compounds according to formula (I) contain at least one group ($CH_2$—$CHR_1$—$O)_x$—H, with $R_1$ is an alkyl or alkenyl moiety having 1 to 22 carbon atoms, which can be saturated or unsaturated, branched or linear, and may be understood therefore as hydroxyalkyl ether derivatives of isosorbide, or $R_1$ can be a hydrogen atom. It is possible that more than one $R_1$-moiety is present in the molecules, according to formula (I).

Preferably, if more than one group $R_1$ is present, the group $R_1$ represents H, and an alkyl moiety containing 1 to 22 carbon atoms. In particular the isosorbide derivatives then contain at least one alkoxide group, such as ethylenoxide and/or propylenoxide groups, $CH_2$—$CH_2$—O or $CH_2$—$CHCH_3$—O, together with end-capped groups of the general structure $CH_2$—$CHR_1$—OH, wherein $R_1$ is an alkyl moiety containing 1 to 22 carbon atoms, and preferably 6 to 18 carbon atoms.

It is possible that both OH-functions of isosorbide are derivatized with said hydroxyalkyl ether groups, or alternatively, only one of them (resulting in a mono-ether derivative of isosorbide). Also, mixed derivatives containing one alkoxide group and one hydroxyalkyl ether group together are encompassed. Most preferred are isosorbide derivatives according to formula (I), in which R' and R" stand for a block copolymer moiety.

The index x represent the degree of polymerization within the moieties $(CH_2—CHR_1—O)_x—H$, and is independently in the range of 1 to 50, whereby, based on the specific alkoxylation process used, the number may be odd or even. The sum of x for the whole molecule therefore ranges from 1 to 100.

The sum of x ranges preferably from 2 to 45, more preferably from 4 to 25, and most preferably from 4 to 10 for alkoxylated groups. If both groups R' and R" are alkoxylated the figure for x in each group R' and R" may be the same or different, whereby those compounds are preferred which have symmetric R' and R" groups, which means the same amount of alkoxide groups in each. Preferred are the ethoxylated isosorbides, i.e. in formula (I) where R stands for a hydrogen atom only. For the case of mixed alkoxylates, the compounds may contain the different alkoxides block-wise or randomized, whereby each group R' and R" may be the same, or different from each other.

The total number of all alkoxylated groups (ethylene oxide, propylene oxide or both) in the inventive isosorbide derivatives ranges from 0 to 100.

The group $R_1$ can also represent a branched or linear, saturated or unsaturated alkyl or alkenyl moiety with 1 to 22 carbon atoms. Preferred are chains from 6 to 18, and 8 to 12 carbon atoms. Also preferred are saturated over unsaturated chains.

The preparation of the compounds according to formula (I) can be carried out by known alkoxylation processes. Thus, to obtain the alkoxylated isosorbides, known methods are applicable. For example, the isosorbide may be reacted with a gaseous alkoxide (ethylene oxide or propylene oxide or blends thereof) in the presence of basic or acidic catalysts under elevated pressure (100-500 kPa) and preferably elevated temperatures, for example in the range of 120 to 220° C. Certain alkoxylated isosorbide derivatives, other than those claimed, are described by S. Ropuszyński and J. Perka, in Wiadomości Chemiczne (1969), Zeszyt 5 (263), pages 297-318.

To obtain the hydroxyalkyl ether derivatives it is most preferred to react isosorbide with an epoxide, selected from ethylene oxide, propylene oxide, or 1,2-alkyloxides according to the general formula $H_2COCH—R_1$, where $R_1$ has the same meaning as in formula (I) above, in the presence of basic catalysts at a temperature from 100 to 200° C., and a pressure in the range from 1 to 10 bar. The reaction leads to a ring opening of the 1,2-alkyloxide to form a hydroxyalkyl ether derivative first. It is possible to carry out the reaction sequence twice, first an ethoxylation step and subsequently a reaction with a long chain alkoxide, preferably 1,2-dodecene oxide or 1,2-decene oxide. As the reaction is a polymerization reaction, the mole ratio isosorbide/1,2-alkylene oxide must not be 1/1, but can differ according to the above definition of x. Useful catalysts are, for example, sodium or potassium hydroxide, or sodium or potassium methylate, which are reacted at a temperature from 100-220° C., especially between 160-200° C.

Specifically preferred compounds include the following:

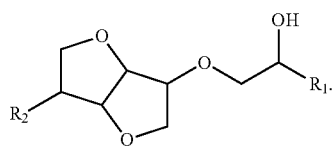

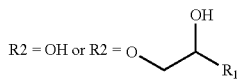

$R_1$ here represents a moiety with 6 to 16 carbon atoms, whereby the chain may be saturated or unsaturated, but is preferably saturated and most preferably also linear. Most preferred is the compound according to the above formula, wherein $R_2$=O—$CH_2$—$CHR_1$—OH.

A second preferred derivative is:

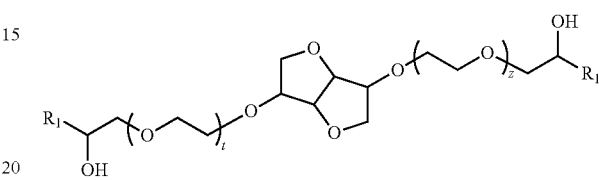

Again, $R_1$ represents a moiety with 6 to 18, but preferably 6 to 16 carbon atoms. The sum of indices z and t is a number between 2 and 50, and is preferably chosen from the numbers 4, 10, 25 or 40. The numbers for the indices z and t may be even or odd numbers. Symmetrical compounds may be of advantage.

Compounds according to formula (I) show cloud points at temperatures between <0° C. up to 60° C. (1% in water), according to the amount of alkoxides groups in the molecule (the more alkoxides the higher the cloud point). The isosorbide derivatives according to the invention also show low foaming behavior.

A further embodiment of the invention pertains to the use of compounds according to formula (I) for the preparation of detergents, cleansers and cosmetic compositions (solid, liquid or gel-like ones). The isosorbide derivatives may be present in amounts from 0.1 up to 80% by weight, dependent on the particular formulation. The isosorbide derivatives are particularly useful in home care applications, like all kind of cleansers (kitchen, bathroom, hard surface, automotive or car cleansers), as well as in dishwashing compositions (hand and automatic dish washing).

The isosorbide derivative may be formulated with other surfactants, including anionic, nonionic, amphoteric and/or cationic surfactants.

The isosorbide derivatives according to the present invention are particularly suitable to be incorporated in detergents and cleaners, including liquid and solid detergents, and preferably for hard surface cleaners, such as kitchen or bathroom cleansers, all purpose cleaners, car wash, or dish washing detergents (for hand washing as well as for automatic dish detergents) and for industrial and institutional cleaning. The use of isosorbide derivatives according to the present invention is particularly preferred in applications where the good low- or de-foaming properties of these compounds are of advantage. Examples of such applications include, without limitation, automatic dishwashing detergents, spray cleaners, bottle cleaning, automotive and locomotive cleaning, high pressure cleaning, and tank cleaning.

The isosorbide derivatives are also suitable in cosmetic preparations, where they can act as emulsifiers, solubilizers, cleaners, rheology modifiers, and/or stabilizers, for rinse-off as well as for leave-on applications.

The isosorbide derivatives are also suitable for agrochemical preparations, especially for spray applications, where they can act as surfactants, emulsifiers, dispersants, foam regulators, rheology modifiers, or as general formulation aids and/or performance enhancers.

EXAMPLES

Preparation of the Isosorbide Derivatives

Example I 1 mole of isosorbide (146 g) is reacted with 1 or 3 moles (156 or 312 g) of 1,2-deceneoxide in the presence of catalytic amounts of KOH (0.025 moles, 1.4 g) at a temperature in the range of 160-180° C. under a nitrogen atmosphere. After completion of the reaction, which can be determined by epoxide titration according to Jay (see for details of the method: Jay et al., *Anal. Chem.*, Volume 36, 1964, page 667), the product is cooled and neutralized by adding adequate amounts of lactic acid. The epoxide value should be reduced to at least 1/10 to 1/20 of the starting value in order to obtain a yield which is at least 90% to 95%.

Example II 1 mole of isosorbide (146 g) is reacted with 4, 10, 25 or 40 moles of ethylene oxide (176, 440, 1100 or 1760 g) in the presence of catalytic amounts of KOH (0.025 moles, 1.4 g) at a temperature in the range of 160-180° C. in a pressure reactor at a maximum pressure of 5 bar. After completion of this reaction, 2 moles of 1,2-dodeceneoxide (386 g) are added and reaction is continued at a temperature in the range of 180-200° C., and is monitored by epoxide titration according to Jay. The product is cooled and neutralized by adding adequate amounts of lactic acid. The epoxide value should be reduced to at least 1/10 to 1/20 of the starting value in order to obtain a yield which is at least 90% to 95%.

Performance Tests of the Isosorbide Derivatives

The cleaning performance of two selected candidates according to example II (with 4 and 10 moles ethylene oxide, respectively) was tested at 25° C. in a modified Gardner test on polyvinyl chloride (PVC) with a standard soil (IPP Soil for diluted applications; 1% active matter).

Testing of the cleaning effect (Gardner Test): The cleaning preparation was applied to an artificially soiled plastic sheet. The 26×28 cm test surface was uniformly coated with 2 g of the artificial soil using a surface spreader and the sheet was then cut up into seven equal pieces measuring 26×4 cm. A plastic sponge was impregnated with 6 ml of the undiluted cleaning solution to be tested, and moved by machine over the test surface. After 10 wiping movements, the cleaned test surface was held under running water and the loose soil removed. The cleaning effect, i.e. the whiteness of the plastic surface thus cleaned, was measured using a Dr. B. Lange LF 90 photoelectric colorimeter. The clean white plastic surface was used as the whiteness standard. The reflectance values are 66 and 71% (for the 4 and the 10 moles product), which is comparable or better to known low foaming surfactants. Examples of low foaming surfactants are DEHYPON® LS 45, DEHYPON® LT 104 and DEHYPON® LS 24 (all products of Cognis GmbH), which give a reflectance of 58%, 57.5% and 49% respectively, according to this test.

What is claimed is:

1. An isosorbide derivative represented by formula (1):

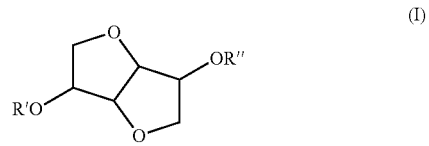

(I)

wherein R' is hydrogen and R" is the polymeric ether moiety $(CH_2-CHR_1-O)_x-H$, where $R_1$ represents hydrogen, or an alkyl moiety having 1 to 33 carbon atoms, which is saturated or unsaturated, branched or linear or an alkenyl moiety having 2 to 33 carbon atoms, which is saturated or unsaturated, branched or linear, and x is a number from 1 to 50.

2. The isosorbide derivative of claim 1, wherein $R_1$ is selected from the group consisting of linear alkyl moieties having 6 to 18 carbon atoms.

3. The isosorbide derivative of claim 2, wherein said linear alkyl moieties have 8 to 12 carbon atoms.

4. The isosorbide derivative of claim 1, wherein x is a number from 2 to 40.

5. The isosorbide derivative of claim 1, wherein x is a number from 4 to 10.

6. A process for the preparation of isosorbide derivatives represented by formula (I)

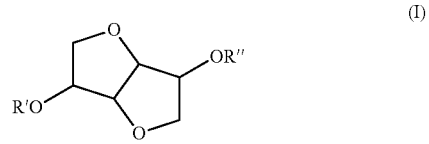

(I)

comprising the step of reacting isosorbide with an epoxide selected from ethylene oxide, propylene oxide, or 1,2-alkyloxides of formula $H_2COCH-R_1$ to form the compound of Formula (I) wherein R' is hydrogen and R" is the polymeric ether moiety $(CH_2-CHR_1-O)_x-H$, where $R_1$ represents an alkyl moiety having 1 to 33 carbon atoms, which is saturated or unsaturated, branched or linear or an alkenyl moiety having 2 to 33 carbon atoms, which is saturated or unsaturated, branched or linear, and x is a number from 1 to 50, in the presence of a basic catalyst at a temperature from 100 to 200° C., and a pressure from 1 to 10 bar.

7. The isosorbide derivative of claim 1, incorporated in a detergent or cleanser composition.

8. The isosorbide derivative of claim 1, incorporated in a cosmetic composition.

9. The isosorbide derivative of claim 1, incorporated in an agrochemical composition.

* * * * *